(12) United States Patent
Harada et al.

(10) Patent No.: US 7,872,755 B2
(45) Date of Patent: Jan. 18, 2011

(54) INTERFEROMETER

(75) Inventors: Ken Harada, Wako (JP); Tetsuya Akashi, Fujimi (JP); Yoshihiko Togawa, Wako (JP); Tsuyoshi Matsuda, Wako (JP); Noboru Moriya, Wako (JP)

(73) Assignee: Riken, Saitama (JP)

( * ) Notice: Subject to any disclaimer, the term of this patent is extended or adjusted under 35 U.S.C. 154(b) by 702 days.

(21) Appl. No.: 11/883,568

(22) PCT Filed: Jan. 27, 2006

(86) PCT No.: PCT/JP2006/301330

§ 371 (c)(1),
(2), (4) Date: Aug. 2, 2007

(87) PCT Pub. No.: WO2006/082758

PCT Pub. Date: Aug. 10, 2006

(65) Prior Publication Data

US 2009/0273789 A1 Nov. 5, 2009

(30) Foreign Application Priority Data

Feb. 3, 2005 (JP) .............................. 2005-027274

(51) Int. Cl.
*G01B 9/02* (2006.01)
(52) U.S. Cl. ..................................................... 356/450
(58) Field of Classification Search .................. 356/450
See application file for complete search history.

(56) References Cited

U.S. PATENT DOCUMENTS

| 2002/0084412 | A1 | 7/2002 | Tomita |
| 2003/0160969 | A1 | 8/2003 | Endo et al. |

FOREIGN PATENT DOCUMENTS

| JP | 2002-117800 | 4/2002 |
| JP | 2005-197165 | 7/2005 |

(Continued)

OTHER PUBLICATIONS

Harada et al. "Double-biprism electron interferometry", Applied Physics Letters, vol. 84, No. 17, pp. 3229-3231.*

(Continued)

*Primary Examiner*—Patrick J Connolly
(74) *Attorney, Agent, or Firm*—Nixon & Vanderhye, P.C.

(57) ABSTRACT

A double-biprism electron interferometer is an optical system which dramatically increases the degree of freedom of a conventional one-stage electron interferometer. The double biprism interferometer, however, is the same as the optical system of the single electron biprism in terms of the one-dimensional shape of an electron hologram formed by filament electrodes, the direction of an interference area, and the azimuth of the interference fringes. In other words, the longitudinal direction of the interference area is determined corresponding to the direction of the filament electrodes, and the azimuth of the interference fringes only coincides with and is in parallel with the longitudinal direction of the interference area. An interferometer according to the present invention has upper-stage and lower-stage electron biprisms, and operates with an azimuth angle Φ between filament electrodes of the upper-stage and lower-stage electron biprisms to arbitrarily control an interference area and an azimuth θ of the interference fringes formed therein.

9 Claims, 11 Drawing Sheets

FOREIGN PATENT DOCUMENTS

JP         2007-115409      5/2007
WO     WO 01/75394 A1    10/2001

OTHER PUBLICATIONS

International Search Report for PCT/JP2006/301330 mailed May 16, 2006.

Harada et al., "High-Resolution observation by double-biprism electron holography", Journal of Applied Physics, vol. 96, No. 11, pp. 6097-6102 (2004).

Harada et al., "Double-biprism electron interferometry", Applied Physics Letters, vol. 84, No. 17, pp. 3229-3231 (2004).

\* cited by examiner

φ = −30°

φ = −15°

φ = ±0°

φ = 10°

φ = 20°

φ = 30°

φ = 40°

φ = 50°

φ = 60°

φ = 70°

INTERFEROMETER

This application is the US national phase of international application PCT/JP2006/301330 filed 27 Jan. 2006 which designated the U.S. and claims benefit of JP 2005-027274, dated 3 Feb. 2005, the entire content of which is hereby incorporated by reference.

TECHNICAL FIELD

The present invention relates to an interferometer having two biprisms and using a charged particle beam such as an electron or an ion, or an interferometer having two optical biprisms and using a light beam.

BACKGROUND ART

The present inventors have developed and have introduced a double-biprism electron interferometer. See, e.g., Japanese Patent Application No. 2004-004156 and Japanese Patent Application No. 2004-102530 In such double-biprism electron interferometer, two electron biprisms are arranged in order of the traveling direction of an electron beam on an optical axis in such a manner that the upper-stage biprism is located on an image plane of a specimen observed and that the lower-stage biprism is located in the shadow area of the upper-stage biprism and potentials applied to their respective filament electrodes are changed so that an overlap area (corresponding to an interference area width W) and an overlap angle (corresponding to an interference fringe spacing s) of two electron waves (e.g., an object wave and a reference wave) can be changed arbitrarily. The upper-stage electron biprism is located on the image plane of the specimen, making it possible to prevent generation of Fresnel fringes superimposed on an interference area such as a hologram, which cannot be removed, in principle, in an electron interferometer using one electron biprism (see, for instance, Japanese Patent Application Laid-open Publication No. 2002-117800). Non-Patent Documents authored by one or more inventors include "Double-Biprism Electron Interferometory". Ken Harada. Tetsuya Akashi. Yoshihiko Togawa, Tsuyoshi Matsuda and Akira Tonomura. Applied Physics Letter: Vol. 84. No. 17, (2004) pp. 3229-3231: and "High-Resolution Observation by Double-Biprism Electron. Holography", Ken Harada, Tsuyoshi, Matsuda, Tetsuya Akashi, Yoshihiko Togawa and Akira Tonomura, Journal of Applied Physics: Vol. 96, No. 11, (2004) pp. 6097-6102.

There is an interferometer using a charged particle beam such as an electron or an ion or an optical interferometer using light.

A double-biprism interferometer has the same optical system as the one-stage electron biprism in terms of the one-dimensional shape of an electron hologram formed by filament electrodes, the direction of the interference area and the azimuth of the interference fringes. In other words, the longitudinal direction of the interference area is determined corresponding to the direction of the filament electrodes, and the azimuth of the interference fringes only coincides with and is in parallel with the longitudinal direction of the interference area.

When a specimen in a shape extending in one direction like a carbon nanotube is observed, the specimen (tube) and interference fringes need to be angled. It is difficult to observe the specimen in the longitudinal direction. Only a part of its elongated shape is observed by means of electron holography (for example, J. Cumings et al., PRL 88, (2002) 056804)). At present, to observe the specimen in the longitudinal direction, some divided holograms of the specimen are recorded and reproduced for synthesis, or a hologram of a wide interference area is recorded without sufficient coherence of electron beams and noise by deteriorated coherence is compensated by image processing.

In addition to independent control of two parameters of the interference area width W and the interference fringe spacing s, an interferometer which can easily observe a specimen in the longitudinal direction by a simple operation is required.

SUMMARY

An interferometer according to the technology disclosed herein has upper-stage and lower-stage electron biprisms, and operates the projection azimuth angle $\Phi$ between filament electrodes of the upper-stage and lower-stage electron biprisms onto an image plane (hereinafter, simply described as an azimuth angle $\Phi$), to arbitrarily control an interference area and the azimuth $\theta$ of the interference fringes formed therein. The double-biprism electron interferometer described in conjunction with the technology disclosed herein is an optical system which dramatically increases the degree of freedom of a one-stage electron interferometer. Primarily an interferometer using an electron is described herein.

The technology disclosed herein includes independent control of two parameters of an interference area width W and an interference fringe spacing s. The technology disclosed herein makes it is possible to easily observe a specimen in the longitudinal direction by controlling the azimuth $\theta$ of the interference fringes.

The technology disclosed herein operates the azimuth angle $\Phi$ between filament electrodes of upper-stage and lower-stage electron biprisms to arbitrarily control an interference area and the azimuth $\theta$ of the interference fringes formed therein. An interferometer having upper-stage and lower-stage electron biprisms as a basis of the technology disclosed herein will be described.

BRIEF DESCRIPTION OF THE DRAWINGS

FIG. 4 FIGS. 4(A) to 4(J) are the experimental results of interference fringe formation obtained by changing the azimuth angle $\Phi$ of the filament electrode $9b$ of the lower-stage electron biprism with reference to the filament electrode $9u$ of the upper-stage electron biprism as X-axis.

DETAILED DESCRIPTION

Figure 1:
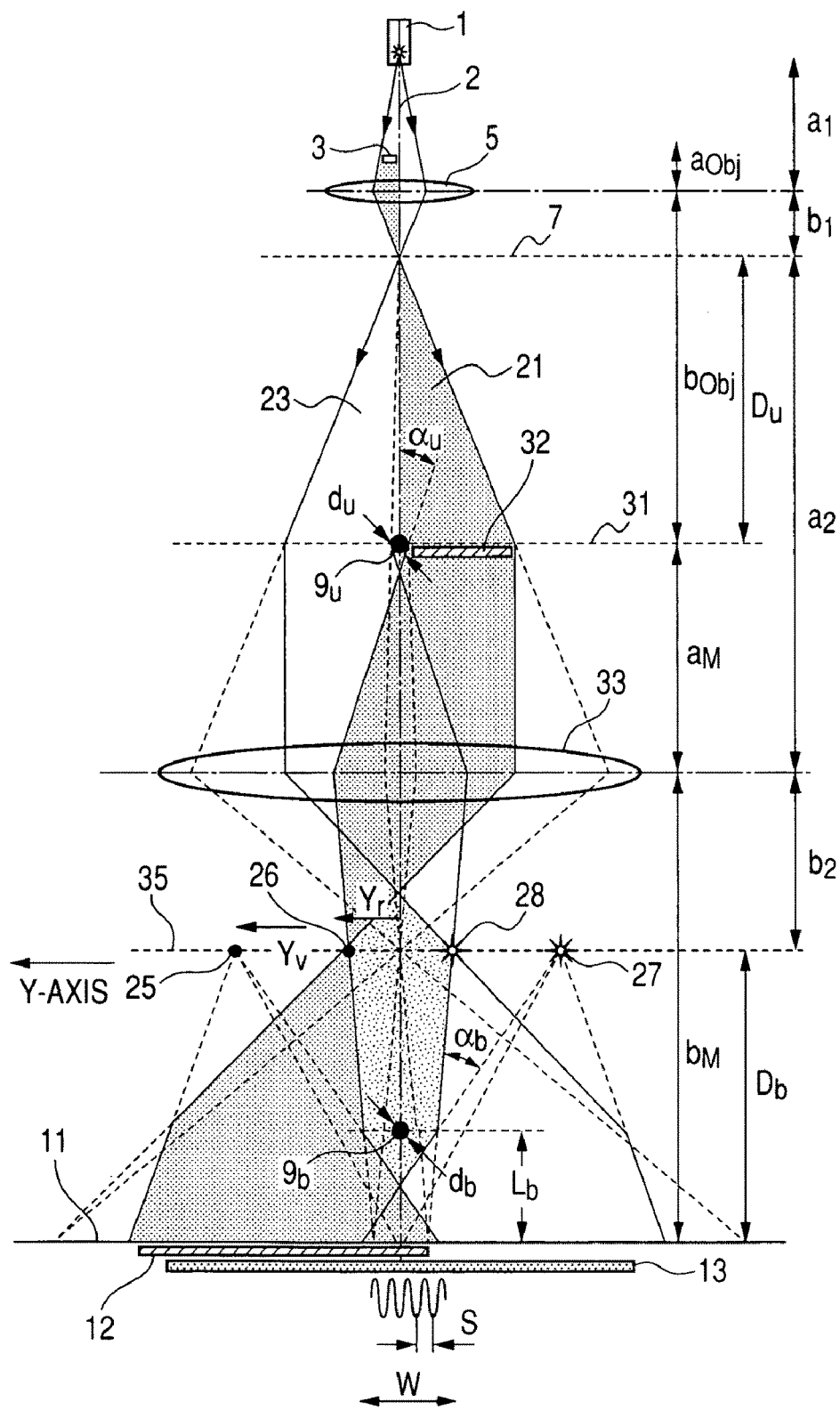
FIG. 1 is a schematic diagram showing an interference optical system using electron biprisms explained in FIG. 3 of Japanese Patent Application No. 2004-004156.
Figure 3:
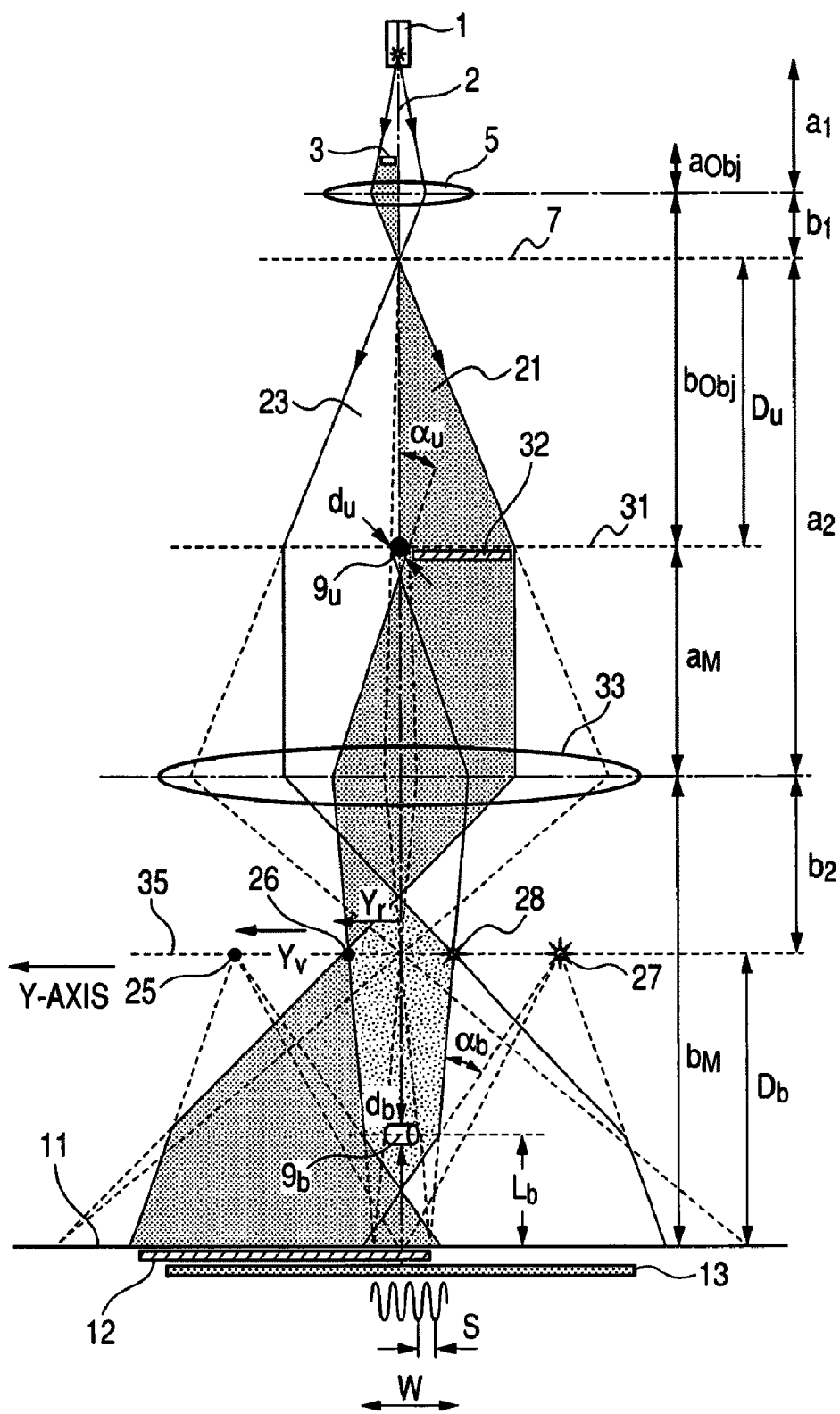
FIG. 3 is a schematic diagram showing an optical system operating with the azimuth angle $\Phi$ between the filament electrodes $9u$ and $9b$ of the upper-stage and lower-stage electron biprisms explained in FIG. 2 in a shown form corresponding to FIG. 1.

FIG. 1 is a schematic diagram showing an interference optical system using the electron biprisms explained in FIG. 3 of Japanese Patent Application No. 2004-004156.

In FIG. 1, the reference numeral 1 denotes an electron source, the reference numeral 2 denotes an optical axis, the reference numeral 3 denotes a specimen, the reference numeral 5 denotes an objective lens system having one or more lenses (In the drawing, for simplification, one equivalent lens is represented. Distances $a_1$ and $b_1$ above and below the equivalent lens correspond to the same and are different from the actual size of the apparatus. This is the same for the drawings after FIG. 1.), the reference numeral 7 denotes a first image plane of an electron source just above the upper-stage electron biprism, the reference numeral 11 denotes an observation plane, the reference numeral 12 denotes a specimen image on the observation plane, and the reference numeral 13 denotes an image recording mean such as a film or a camera. The reference numerals 21 and 23 denote an object wave and a reference wave. The reference numeral 31 denotes an image plane of a specimen determined by the objective lens system 5, the reference numeral 32 denotes a specimen image by the objective lens system 5, the reference numeral 33 denotes a magnifying lens, the reference numeral 35 denotes an image plane of an electron source by the magnifying lens 33, and the reference numeral $9_u$ denotes a filament electrode of the upper-stage electron biprism located on the image plane of the specimen 31 by the objective lens system 5 and has a diameter $d_u$. The reference numeral $9_b$ denotes a filament electrode of the lower-stage electron biprism located between the image plane of the electron source 35 by the magnifying lens 33 and the observation plane 11 and has a diameter $d_b$. The interference fringe spacing s and the interference area width W appearing on the observation plane 11 are schematically shown under the recording means 13. Here, the electron source 1 is shown in a single block in the drawing, and includes a source, an acceleration tube, and a condenser optical system. The electron biprism of the schematic diagram shown here is of the electric field type, has a filament electrode of an extrafine wire at the center and grounding electrodes on the right and left sides of the outside far the portion through which an electron beam passes, and applies a voltage to the filament electrode at the center to deflect the electron beam. In FIG. 1 and the drawings thereafter, the cross section or the end section of the filament electrode at the center is indicated by a small circle. In the description noting the function of the electron biprism, only the electron biprism is represented. In the description of the filament electrode at the center, the filament electrode of the electron biprism is represented. An electron optical system typically uses an electromagnetic lens as an electron lens, and includes rotation about an axis in parallel with the optical axis in the path of the electron beam. FIG. 1 neglects rotation of the electron beam by the electromagnetic lens and shows an electron optical system on the same plane. This is the same for the drawings showing the optical system after FIG. 1.

An electron beam emitted from the electron source 1 is split into the object wave 21 passing through the specimen 3 located on one side of the optical axis 2 and the reference wave 23 passing through the side without the specimen 3. To easily identify the object wave 21 and the reference wave 23, only the area of the object wave 21 is patterned. The object wave 21 and the reference wave 23 are refracted on the objective lens system 5 to cross on the image plane of the electron source 7 just above the upper-stage electron biprism for traveling to the magnifying lens 33. The object wave 21 and the reference wave 23 form the specimen image 32 on the image plane of the specimen 31 by the objective lens system 5 and pass through the position of the upper-stage electron biprism on the image plane 31. Both the electron beams of the object wave 21 and the reference wave 23 are deflected toward the optical axis 2 by an applied voltage $V_u$ to the filament electrode $9_u$ of the upper-stage electron biprism. Two split real images of an electron source 26 and 28 are formed on the downstream side of the magnifying lens 33. Both the electron beams of the object wave 21 and the reference wave 23 are deflected again by an applied voltage $V_b$ to the filament electrode $9_b$ of the lower-stage electron biprism and form virtual images of an electron source 25 and 27. $Y_r$ is a split distance from the optical axis to the real source 26 caused by the deflection by the filament electrode $9_u$ of the upper-stage electron biprism, and $Y_v$ is a split distance from the real image of the electron source 26 to the virtual source 25 caused by the deflection by the filament electrode $9_b$ of the lower-stage electron biprism. They are expressed as Equations (1) and (2) as follows.

$$Y_r = \frac{b_2}{a_2} \cdot \alpha_u (b_{obj} - b_1) = \frac{1}{M_{obj}} \cdot \alpha_u D_u \quad \text{[Equation 1]}$$

$$Y_v = \alpha_b (b_M - b_2 - L_b) = \alpha_b (D_b - L_b) \quad \text{[Equation 2]}$$

The observation plane 11 is an image plane of the filament electrode $9_u$ of the upper-stage electron biprism. The deflection by the upper-stage electron biprism does not influence the image formation and overlap of the wavefront does not occur. As real deflection of the electron beam, however, is performed, the splits of the real electron-source images 26 and 28 occur. This is essentially the same as the splits of the virtual electron source images 25 and 27 by the filament electrode $9_b$ of the lower-stage electron biprism.

The interference fringes backprojected onto the object plane of the objective lens system 5 where the specimen is positioned when both the electron biprisms simultaneously work in the configuration shown in FIG. 1 are expressed as Equations (3) and (4). $M_{Obj}$ is a magnification by the objective lens system 5 to the specimen 3, and $M_M$ is a magnification by the magnifying lens 33 to the specimen image 32. The interference fringe spacing s and the interference area width W backprojected onto the object plane are expressed by a subscript Obj.

$$S_{obj} = \frac{a_M}{b_M} \cdot \frac{a_{obj}}{b_{obj}} \cdot \frac{D_b \lambda}{(Y_v + Y_r)} = \quad \text{[Equation 3]}$$

$$\frac{1}{M_M} \cdot \frac{1}{M_{obj}} \cdot \frac{D_b \lambda}{2\left\{\left(\frac{b_2}{a_2} D_u \alpha_u\right) + (D_b - L_b)\alpha_b\right\}} =$$

$$\frac{1}{M_M} \cdot \frac{1}{M_{obj}} \cdot \frac{a_2 D_b \lambda}{2\{\alpha_b a_2 (D_b - L_b) + \alpha_u b_2 D_u\}}$$

-continued $$W_{obj} = \frac{a_M}{b_M} \cdot \frac{a_{obj}}{b_{obj}} \cdot \frac{2Y_v L_b}{D_b - L_b} - \frac{a_{obj}}{b_{obj}} d_u = \frac{1}{M_M} \cdot \frac{1}{M_{obj}} \cdot 2\alpha_b L_b - \frac{1}{M_{obj}} d_u$$ [Equation 4]

Equations (3) and (4) mean that the interference area width $W_{Obj}$ is not dependent on a deflection angle $\alpha_u$ by the upper-stage electron biprism. This makes it possible to independently control the interference fringe spacing $s_{Obj}$ and the interference area width $W_{Obj}$. To be more specific, independent operation can be done by the following procedure:

(1) The lower-stage electron biprism→The interference area width $W_{Obj}$ is determined.

(2) The upper-stage electron biprism→The interference fringe spacing $s_{Obj}$ is adjusted.

One of the optical conditions, (Db–Lb=0), means that the filament electrode 9b of the lower-stage electron biprism is placed in the position of the image plane of the electron source 35 by the magnifying lens 33. In this case, in Equation (3), the interference fringe spacing sObj is not dependent on a deflection angle αb by the lower-stage electron biprism. Under the optical conditions, perfectly independent control of the interference fringe spacing sObj and the interference area width WObj can be done using both the biprisms.

In Japanese Patent Application No. 2004-004156, the electron interferometer which can independently control the interference fringe spacing $s_{Obj}$ and the interference area width $W_{Obj}$ can be realized. The one-dimensional shape of an electron hologram formed by the filament electrodes, the direction of the interference area, and the azimuth of the interference fringes are the same as the optical system of the one-stage electron biprism. The longitudinal direction of the interference area is determined corresponding to the direction of the filament electrodes and the azimuth of the interference fringes coincides with and is in parallel with the longitudinal direction of the interference area.

An interferometer according to the technology disclosed herein has upper-stage and lower-stage electron biprisms, and operates with the azimuth angle Φ between filament electrodes of the upper-stage and lower-stage electron biprisms to arbitrarily control the interference area and the azimuth θ of the interference fringes formed therein.

Figure 2:
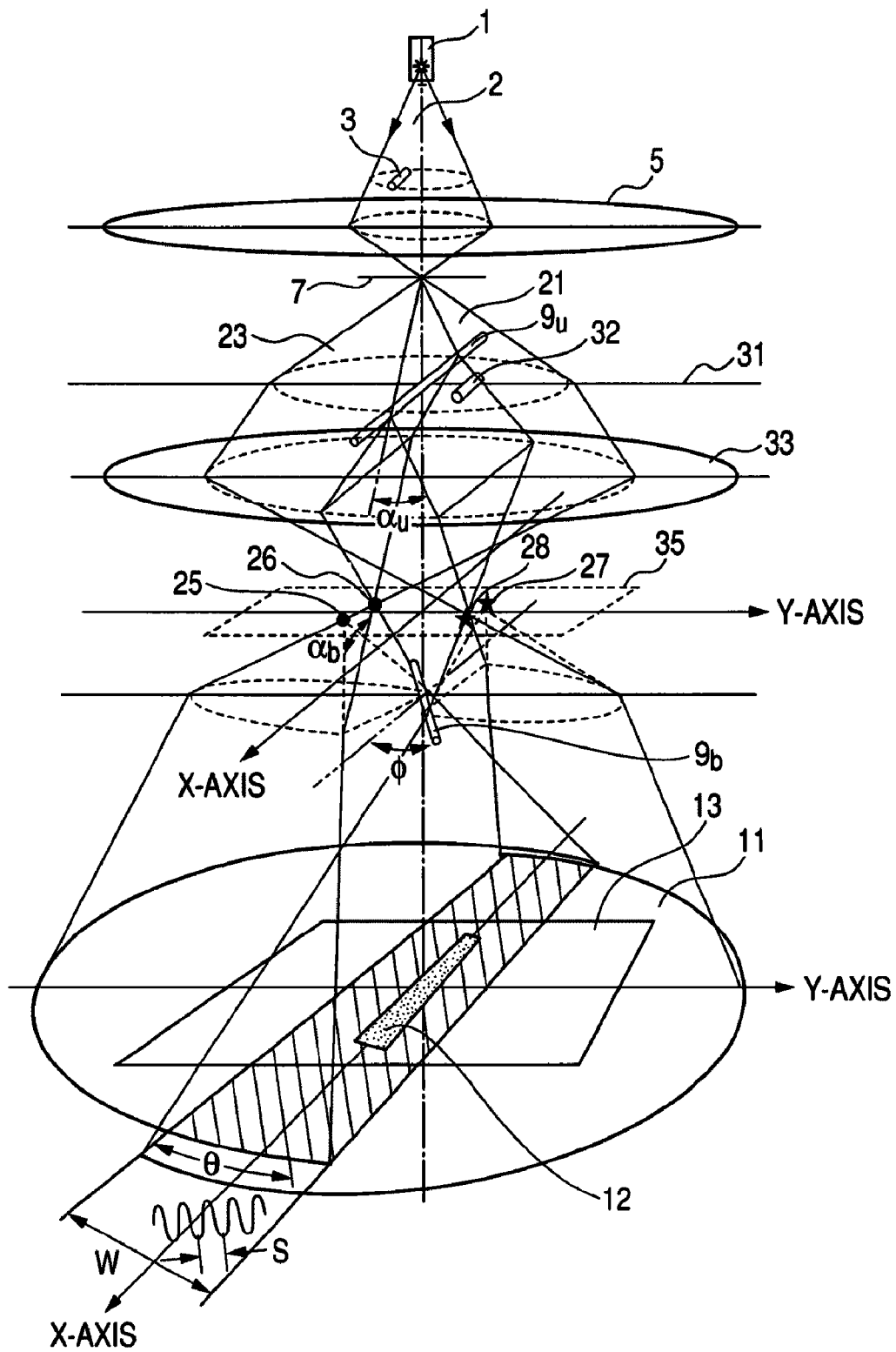
FIG. 2 is a schematic diagram of an optical system operating with an azimuth angle $\Phi$ between filament electrodes of upper-stage and lower-stage electron biprisms for explaining formation of interference fringes.

FIG. 2 is a schematic diagram explaining the formation of interference fringes obtained by an optical system with the azimuth angle Φ between filament electrodes of upper-stage and lower-stage electron biprisms. FIG. 2 schematically shows an optical system corresponding to FIG. 1 and shows a three-dimensional structure to easily understand the azimuth angle Φ between the filament electrodes of the upper-stage and lower-stage electron biprisms. FIG. 3 is also a schematic diagram showing an optical system with the azimuth angle Φ between the filament electrodes $9_u$ and $9_b$ of the upper-stage and lower-stage electron biprisms explained in FIG. 2 in a shown form corresponding to FIG. 1. The filament electrode $9_b$ of the lower-stage electron biprism is drawn in the landscape-orientation to show that there is the azimuth angle Φ between the filament electrode $9_b$ of the lower-stage electron biprism and the filament electrode $9_u$ of the upper-stage electron biprism. The two real electron-source images 26 and 28 and the virtual electron-source images 25 and 27 are projected onto the same plane (on the sheet) to be drawn and the depth is omitted.

In FIG. 2, the filament electrode $9_u$ of the upper-stage electron biprism coincides with X-axis. Those corresponding to the components shown in FIG. 1 are indicated by the same reference numerals in FIGS. 2 and 3. An ellipse indicated by a dashed line of FIG. 2 schematically shows the position of one wavefront in each position. A square indicated by a dashed line schematically shows the image plane of the electron source 35.

The relation between the azimuth angle θ between the filament electrodes $9_u$ and $9_b$ of the upper-stage and lower-stage electron biprisms and the azimuth θ of the interference fringes obtained is changed by the arrangement of the optical system and is changed by the potential applied to the upper-stage filament electrode. This is led by geometric optics. The relational equations of the optical system according to the embodiment are expressed as Equations (5), (6), and (7). Equations (5), (6), and (7) show the relation projected onto the object plane where the specimen is positioned. The letters in the equations are as described in FIGS. 1 to 3 and the above description.

$$S_{obj} = \frac{a_M}{b_M} \cdot \frac{a_{obj}}{b_{obj}} \cdot \frac{D_b \lambda}{2\sqrt{\left(\frac{b_2}{a_2}D_u\alpha_u\right)^2 + (D_b - L_b)^2\alpha_b^2 + 2\left(\frac{b_2}{a_2}D_u\alpha_u\right)(D_b - L_b)\alpha\cos\Phi}} =$$

$$\frac{1}{M_M} \cdot \frac{1}{M_{obj}} \cdot \frac{D_b\lambda}{2\sqrt{Y_r^2 + (D_b - L_b)^2\alpha_b^2 + 2Y_r(D_b - L_b)\alpha\cos\Phi}}$$ [Equation 5]

$$W_{obj} = \frac{a_M}{b_M} \cdot \frac{a_{obj}}{b_{obj}} \cdot \frac{2Y_v L_b}{D_b - L_b} \cdot \cos\Phi - \frac{a_{obj}}{b_{obj}} d_{u=} \frac{1}{M_M} \cdot \frac{1}{M_{obj}} \cdot 2\alpha_b L_b \cdot \cos\Phi - \frac{1}{M_{obj}} d_u$$ [Equation 6]

$$\theta_{obj} = \text{Tan}^{-2}\left[\frac{(D_b - L_b)\alpha_b\sin\Phi}{\left(\frac{b_2}{a_2}D_u\alpha_u\right) + (D_b - L_b)\alpha_b\sin\Phi}\right] = \text{Tan}^{-2}\left[\frac{(D_b - L_b)\alpha_b\sin\Phi}{Y_r + (D_b - L_b)\alpha_b\sin\Phi}\right]$$ [Equation 7]

By these equations, in the case of the optical system which can independently control the interference area width W and interference fringe spacing s perfectly about the above described, that is, in the case of ($D_b$–$L_b$=0) in which the filament electrode $9_b$ of the lower-stage electron biprism is located on the image plane of the electron source 35, the azimuth θ of the interference fringes recorded onto a hologram is zero regardless of the azimuth angle Φ between the filament electrodes of both the biprisms. This means that the accuracy for adjusting the azimuth angle between the filament electrodes of the two electron biprisms is not much important in the case of the conditions.

FIGS. 4(A) to 4(J) are the experiment results of interference fringe formation obtained by changing the azimuth angle Φ of the filament electrode $9_b$ of the lower-stage electron biprism with reference to the filament electrode $9_u$ of the upper-stage electron biprism as X-axis. The experiment is performed under the conditions that nothing is placed in the position of the specimen, the object wave and the reference wave interfere with each other to form only interference fringes, and the interference area width W is constant. In rotation, minus indicates left rotation (counterclockwise rotation) and plus indicates right rotation (clockwise rotation) in the traveling direction of the electron beam (seen from the upper part of the drawing). For the azimuth angles Φ, FIG.

Figure 4A:
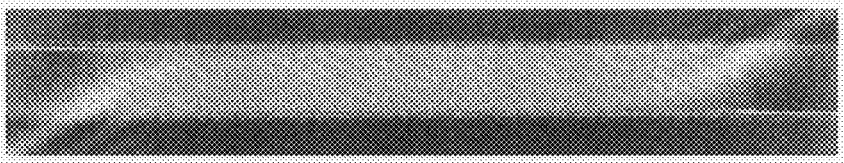
Figure 4B:
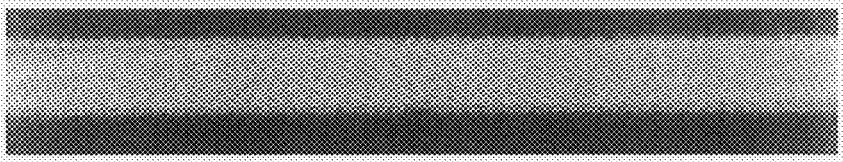
Figure 4C:
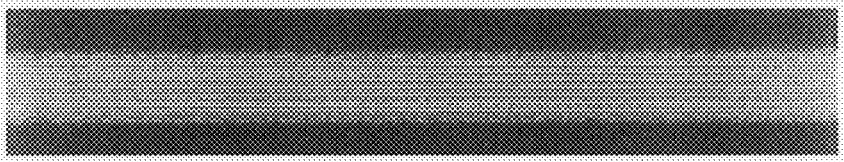
Figure 4D:
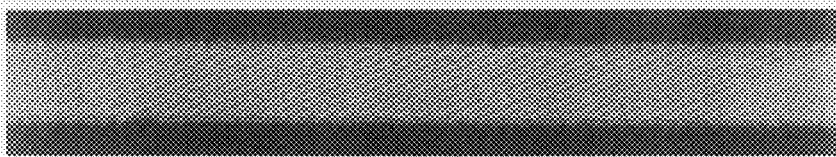
Figure 4E:
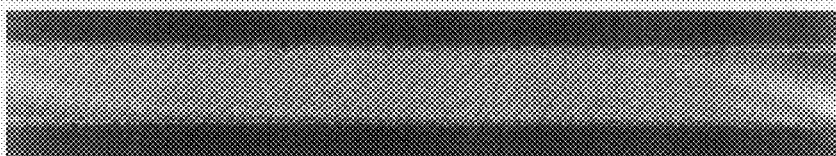
Figure 4F:
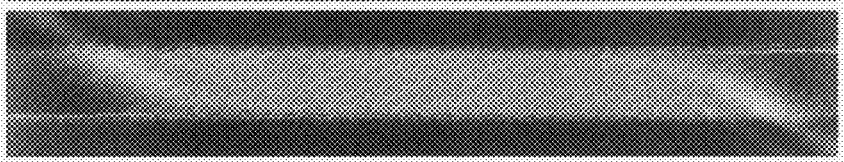
Figure 4G:
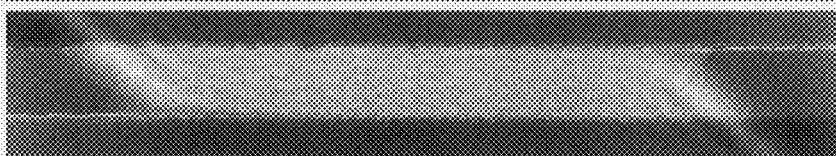
Figure 4H:
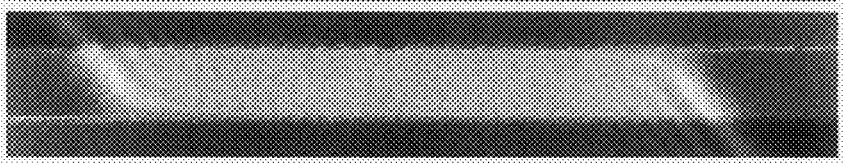
Figure 4I:
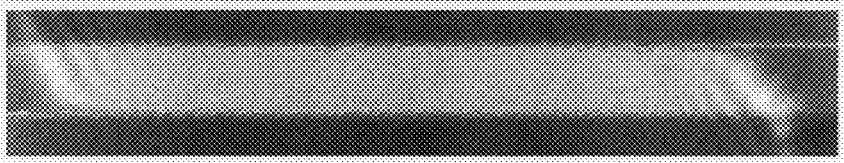
Figure 4J:
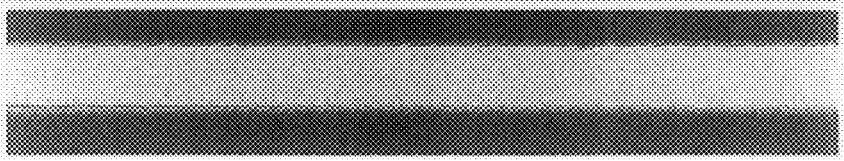

4(A) is Φ=−30°, FIG. 4(B) is Φ=−15°, FIG. 4(C) is Φ=±0°, FIG. 4(D) is Φ=10°, FIG. 4(E) is Φ=20°, FIG. 4(F) is Φ=30°, FIG. 4(G) is Φ=40°, FIG. 4(H) is Φ=50°, FIG. 4(I) is Φ=60°, and FIG. 4(J) is Φ=70°, respectively.

As seen from FIG. 4(C), when the azimuth angle Φ is zero (which coincides with the double-biprism electron interferometer of Japanese Patent Application No. 2004-004156), the interference fringes are in parallel with the longitudinal direction of the specimen. It is difficult to make a hologram showing the characteristic of the specimen changed in the longitudinal direction. As seen by comparing FIG. 4(C), FIG. 4(B), and FIG. 4(D), the filament electrode $9_b$ of the lower-stage electron biprism is rotated in the direction in which the azimuth angle Φ is minus, that is, in the left rotation (counter-clockwise) direction. The interference fringes have an azimuth upward when going left to right. On the other hand, the filament electrode $9_b$ of the lower-stage electron biprism is rotated in the direction in which the azimuth angle Φ is plus, that is, in the right rotation (clockwise) direction. The interference fringes have an azimuth downward when going left to right. When the azimuth angle Φ is increased, the angle of the interference fringes is found to be increased with it.

As seen from FIG. 4(A) and FIGS. 4(E) to 4(J), when the azimuth angle Φ is increased, tilted Fresnel fringes are observed from both ends of the observed area. In this optical system, azimuth rotation is provided to the filament electrode $9_b$ of the lower-stage electron biprism. The ends of the filament electrode $9_b$ of the lower-stage electron biprism do not enter the shadow area of the filament electrode $9_u$ of the upper-stage electron biprism. The Fresnel fringes generated by the filament electrode $9_b$ of the lower-stage electron biprism are superimposed at the both ends of the interference area.

Figure 5A:
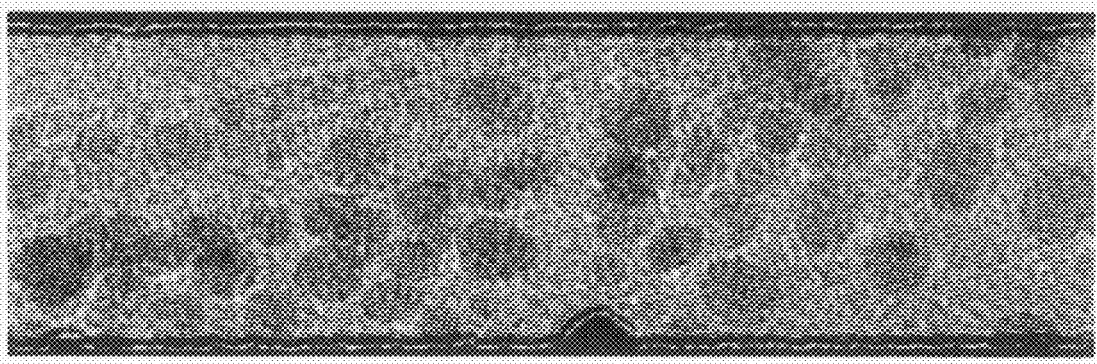
FIGS. 5(A) and 5(B) are examples of electron holograms obtained by appropriately adjusting the observation conditions.
Figure 5B:
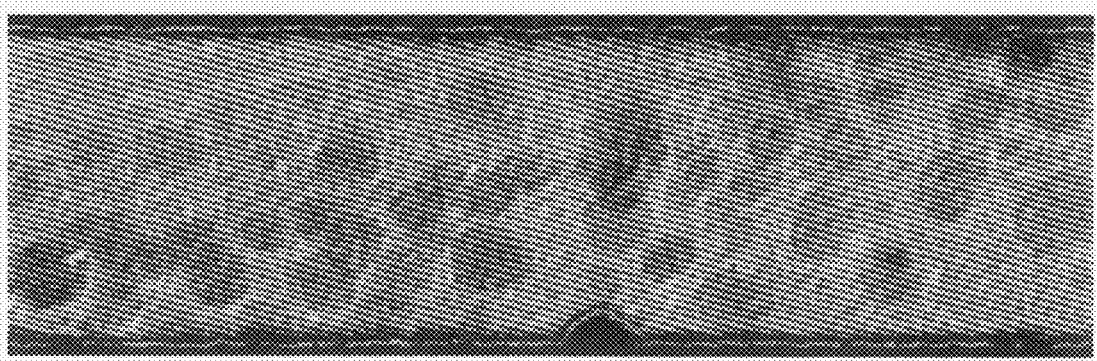

As for contrast of the Fresnel fringes appearing at the both ends of the interference area, the observation conditions such as the potentials applied to the filament electrodes $9_u$ and $9_b$ of both the electron biprisms and the azimuth angle Φ are properly selected to form a hologram having sufficiently small influence. FIGS. 5(A) and 5(B) are holograms obtained by properly selecting the observation conditions. These are holograms of gold particles on the support film made by simulating an elongated specimen. It is found that the same region of the specimen is observed by the particles distribution and that, from the dents of the interference area (the lower parts at the center of the holograms) caused by adhesive contamination onto the upper-stage filament electrode $9_u$, the same portion of the upper-stage filament electrode $9_u$ is used. FIG. 5(A) shows the hologram when the applied voltages $V_u$ and $V_b$ to the filament electrodes $9_u$ and $9_b$ of the upper-stage and lower-stage electron biprisms are $V_u$=100V and $V_b$=59V and the relative azimuth angle Φ is 14°. For the obtained parameter values, the interference area width $W_{Obj}$ is 40 nm, the interference fringe spacing $s_{Obj}$ is 0.55 nm, and the azimuth $\theta_{Obj}$ of the interference fringes is 8°. The sufficiently large azimuth $\theta_{Obj}$ of the interference fringes to the interference area is found to be obtained. FIG. 5(B) shows the hologram when the applied voltage $V_u$ to the filament electrode $9_u$ of the upper-stage electron biprism is $V_u$=0V. The applied voltage $V_b$ to the filament electrode $9_b$ of the lower-stage electron biprism and the relative azimuth angle Φ are the same as FIG. 5(A). For the parameter values obtained in this case, the interference area width $W_{Obj}$ is 40 nm, the interference fringe spacing $s_{Obj}$ is 0.91 nm, and the azimuth $\theta_{Obj}$ of the interference fringes is 14°. When the azimuth angle Φ and the interference area width $W_{Obj}$ are maintained constant, it is found that the interference fringe spacing $s_{Obj}$ and the azimuth $\theta_{Obj}$ of the interference fringes can be changed.

According to the technology disclosed herein, as a parameter treating interference, in addition to the conventional interferometry such as interference area width W and the interference fringe spacing s, the azimuth θ of the interference fringes is added. Control of these parameters is performed by the applied voltages $V_u$ and $V_b$ to the filament electrodes $9_i$ and $9_b$ of the upper-stage and lower-stage electron biprisms and the relative azimuth angle Φ between the filament electrodes of both the electron biprisms when the position of the electron biprisms in the optical system is determined.

To check coincidence of the experimental results shown in FIGS. 4 and 5 with the above-described Equations (1) to (7), Equations (8) and (9) are derived under the conditions in which the interference area width W is fixed to a value of $W_0$.

$$S_{obj} = \frac{a_M}{b_M} \cdot \frac{a_{obj}}{b_{obj}} \cdot \qquad \text{[Equation 8]}$$

$$\frac{D_b \lambda}{2\left\{\begin{array}{c}\left(\frac{b_2}{a_2}D_u\alpha_u\right)^2 + \left(\frac{b_2}{a_2}D_u\alpha_u\right)\left(\frac{D_b - L_b}{L_b}\right) \\ (M_M M_{obj} W_0 + M_M d_u) + \\ \left(\frac{D_b - L_b}{2L_b}\right)^2 (M_M M_{obj} W_0 + M_M d_u)^2 \frac{1}{\cos^2\Phi}\end{array}\right\}^{\frac{1}{2}}} = \frac{1}{M_M} \cdot$$

$$\frac{1}{M_{obj}} \cdot \frac{D_b \lambda}{2\left\{\begin{array}{c}Y_r^2 + Y_r\left(\frac{D_b - L_b}{L_b}\right)\left(\begin{array}{c}M_M M_{obj} W_0 + \\ M_M d_u\end{array}\right) + \\ \left(\frac{D_b - L_b}{2L_b}\right)^2 \left(\begin{array}{c}M_M M_{obj} W_0 + \\ M_M d_u\end{array}\right)^2 \frac{1}{\cos^2\Phi}\end{array}\right\}^{\frac{1}{2}}}$$

$$\theta_{obj} = \mathrm{Tan}^{-1}\left[\frac{\frac{D_b - L_b}{2L_b}(M_M M_{obj} W_0 + M_M d_u)}{\left(\frac{b_2}{a_2}D_u\alpha_u\right) + \frac{D_b - L_b}{2L_b}}\tan\Phi\right] \quad \text{[Equation 9]}$$

$$= \mathrm{Tan}^{-1}\left[\frac{\frac{D_b - L_b}{2L_b}(M_M M_{obj} W_0 + M_M d_u)}{Y_r + \frac{D_b - L_b}{2L_b}(M_M M_{obj} W_0 + M_M d_u)}\tan\Phi\right]$$

Figure 6:
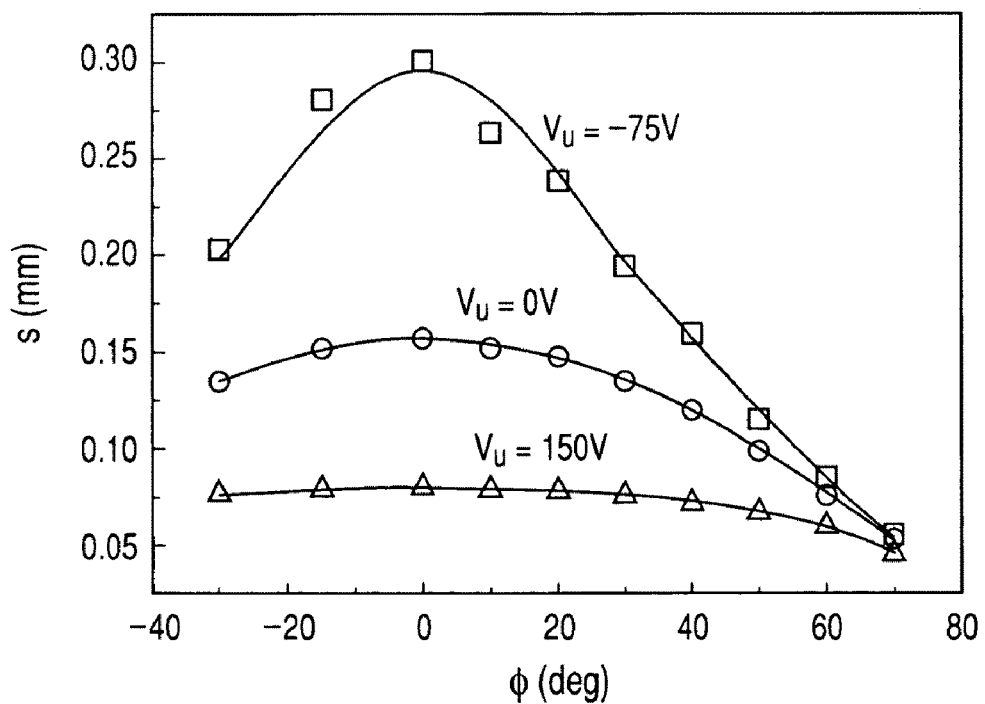
FIG. 6 is a diagram showing the relation between an interference fringe spacing s and the azimuth angle $\Phi$.
Figure 7:
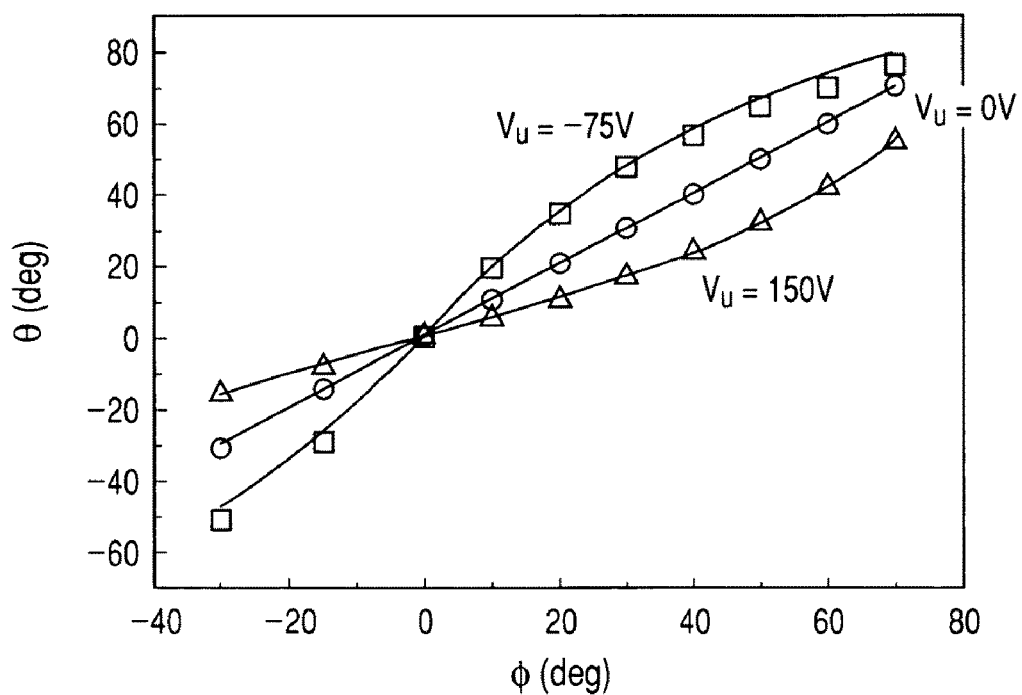
FIG. 7 is a diagram showing the relation between an azimuth $\theta$ of the interference fringes and the azimuth angle $\Phi$.

FIG. 6 shows the relation between the interference fringe spacing s and the azimuth angle Φ obtained from the experimental results in FIG. 4 and under other similar experimental conditions. FIG. 7 shows the relation between the azimuth θ of the interference fringes and the azimuth angle Φ. The azimuth angle Φ is indicated on the horizontal axis, and the interference fringe spacing s and the azimuth θ of the interference fringes are indicated on the vertical axis. In the experimental results indicated by open squares in the both figures, the applied voltage to the filament electrode $9_u$ of the upper-stage electron biprism is $V_u$=−75V. In the experimental results indicated by open circles, the applied voltage to the filament electrode $9_u$ of the upper-stage electron biprism is $V_u$=0V. In the experiment results indicated by open triangles, the applied voltage to the filament electrode $9_u$ of the upper-stage electron biprism is $V_u$=150V. The applied voltage $V_b$ to the filament electrode $9_b$ of the lower-stage electron biprism in the respective cases is selected in such a manner that the interference area width W is 8 mm on a negative film.

The solid curves in FIGS. 6 and 7 are based on Equations (8) and (9). It is found that they are in good agreement with the experiment results.

FIG. 6 shows that when the azimuth angle Φ is zero, the interference fringe spacing s is largest and in rotation of either of the plus and minus directions, the interference fringe spacing s is reduced to be symmetric with the azimuth angle Φ. The rate of reduction in the interference fringe spacing s is different depending on whether the applied voltage to the filament electrode $9_u$ of the upper-stage electron biprism is plus or minus. In FIG. 7, when the azimuth angle Φ is zero, the azimuth θ of the interference fringes is zero and in rotation of either of the plus and minus directions, the azimuth θ of the interference fringes is found to be increased corresponding to the rotation direction. Except that the applied voltage to the filament electrode $9_u$ of the upper-stage electron biprism is zero (the experimental results indicated by circles), the relation between the azimuth angle Φ and the azimuth θ is not linear. As described above, nonlinearity of the interference fringe spacing s and the azimuth angle Φ (FIG. 6) and non-linearity of the azimuth θ and the azimuth angle Φ (FIG. 7) are used so that free control between the interference fringe spacing s and the azimuth θ can be done.

The relation between the interference fringe spacing s and the azimuth θ can be described in a simple form. Equation (10) shows the relation.

$$\frac{\cos\theta_{obj}}{S_{obj}} = \frac{2M_b M_u}{D_b \lambda} \left\{ Y_r + \frac{D_b - L_b}{2L_b}(M_b M_u W_0 + M_b d_u) \right\}$$ [Equation 10]

According to Equation (10), the reciprocal number of the interference fringe spacing s and the cosine value of the azimuth θ are found to be described by the linear function of the distance $Y_r$ from the optical axis to the real images of the electron source 26 and 28. The relation of the left side of Equation (10) is a constant when the applied voltage $V_u$ to the upper-stage electron biprism is not changed.

Figure 8:
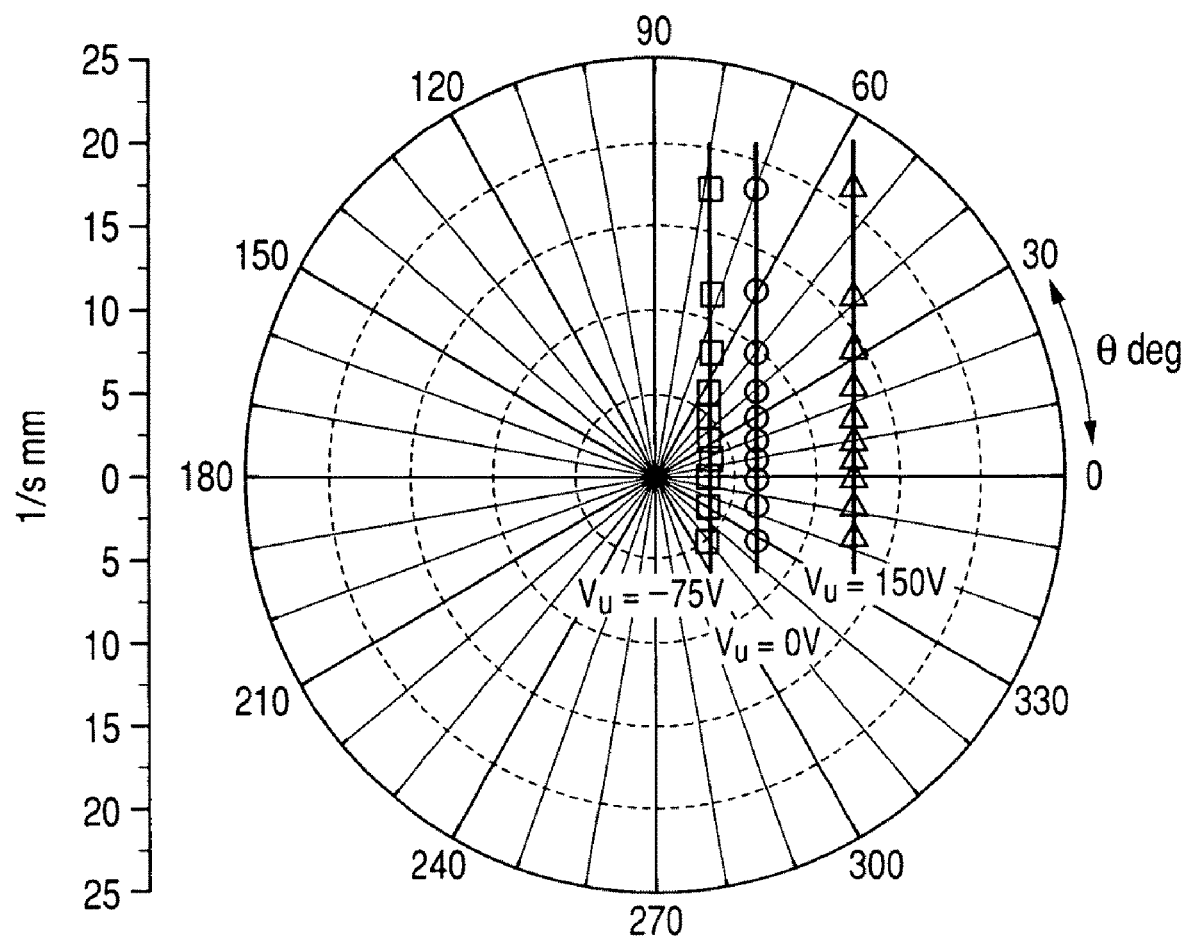
FIG. 8 is a polar net diagram based on the relation of Equation (10).

FIG. 8 is a polar net diagram based on Equation (10) with the experimental results in FIGS. 6 and 7. In the experimental results indicated by open squares similar to the FIGS. 6 and 7, the applied voltage to the filament electrode $9_u$ of the upper-stage electron biprism is $V_u=-75V$. In the experimental results indicated by open circles, the applied voltage to the filament electrode $9_u$ of the upper-stage electron biprism is $V_u=0V$. In the experiment results indicated by open triangles, the applied voltage to the filament electrode $9_u$ of the upper-stage electron biprism is $V_u=150V$. The experimental results are arranged in a vertical straight line on the polar net. As described above, this shows that when the applied voltage $V_u$ to the upper-stage electron biprism is not changed, the left side of Equation (10) is a constant. The interference fringe spacing s and the azimuth θ are linked by a simple relation to make it possible to control mutually and freely.

The above equations are derived about the parameters on the image plane 11 behind the lower-stage electron biprism $9_b$ to easily compare the technology disclosed herein to Japanese Patent Application No. 2004-004156. In a practical and conventional electron microscope, a magnifying lenses and a projection lens are provided at the downstream side of the image plane 11. In this case, the terms of the magnification in the equations are only modified corresponding to the magnification which is given by the additional lenses and the equations themselves are not changed.

Figure 9:
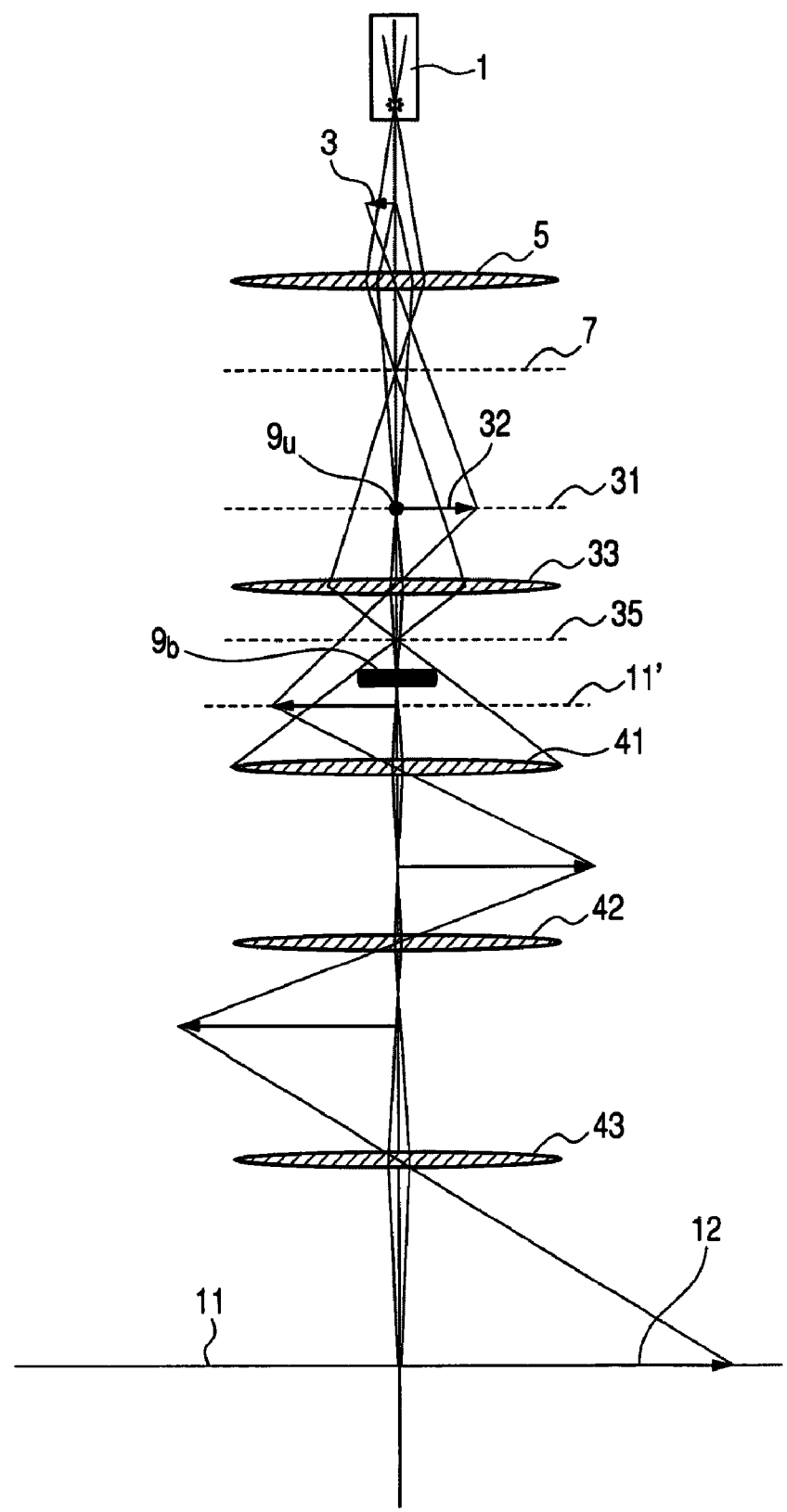
FIG. 9 is a schematic diagram of the optical system composed of additional lenses.

FIG. 9 is a schematic diagram showing the optical system composed of additional lenses, such as a second magnifying lens 41, a third magnifying lens 42, and a projection lens 43 to the system in FIGS. 2 and 3. A specimen image plane 11' by the magnifying lens 33 is also added in FIG. 9 for understanding. The above embodiment (FIGS. 6, 7, and 8) is performed by the optical system as shown in FIG. 9. The interference fringe spacing s are finally magnified values which are recorded on negative films.

According to the technology disclosed herein, optimum interference area for an observation object such as the shape of a specimen, the shape of a portion to be observed, and orientation of the lattice image can be achieved. Furthermore the interference fringes with optimum azimuth are superimposed to the observation object independently. A hologram can be formed and recorded in the optimum state in spatial resolution and phase resolution.

Figure 10A:
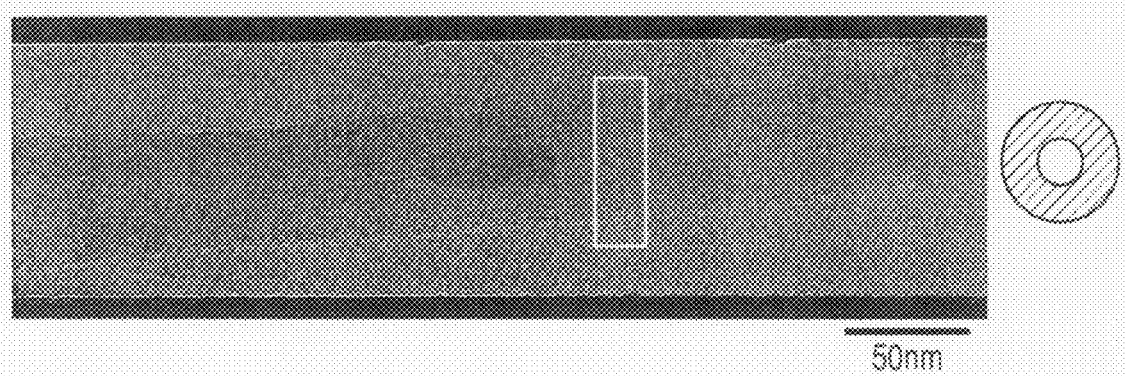
FIGS. 10(A) to 10(E) are experimental results of a carbon nanotube observed by the technology disclosed herein.
Figure 10B:
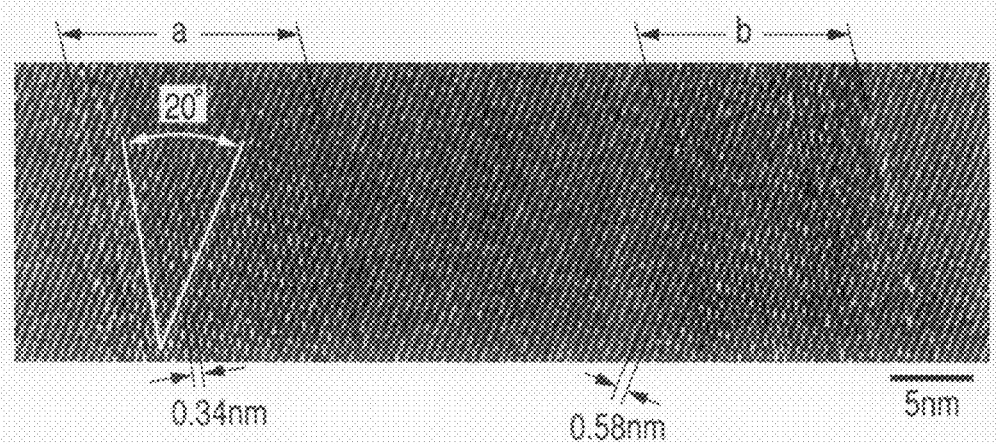
Figure 10C:
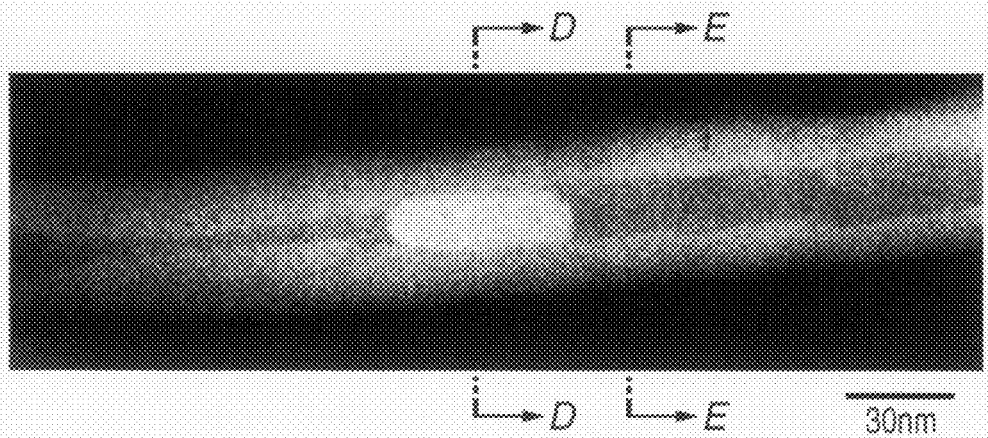
Figure 10D:
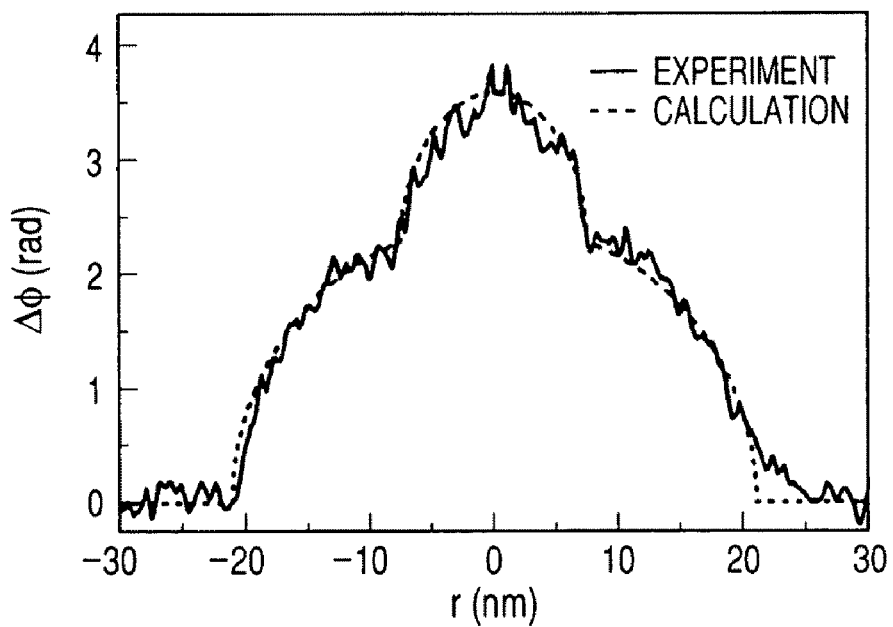
Figure 10E:
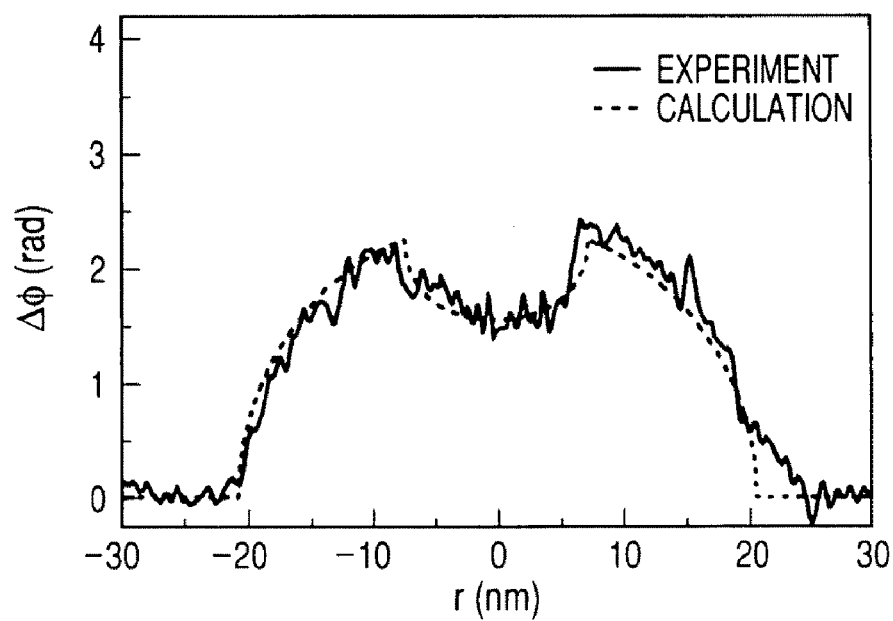

FIGS. 10(A) to 10(E) are experimental results of a carbon nanotube observed by the technology disclosed herein. FIG. 10(A) shows an electron hologram of the carbon nanotube obtained by a transmission electron microscope. Iron particles used as a catalyst for producing the carbon nanotube are observed at the center. The right-outside of the hologram is a cross-sectional drawing of the nanotube which is in a substantially circular shape in the portion surrounded by a square in FIG. 10(A). FIG. 10(B) is an enlarged micrograph of the carbon nanotube at the squared area in FIG. 10(A). For convenience to the eye, the enlarged micrograph is rotated 90° and is shown in landscape-orientation. Graphite walls in both side of the carbon nanotube are indicated by the reference numerals a and b (another part from a and b is the vacuum area outside the tube or the hollow portion in the tube). The lattice spacing of a graphite layer in carbon nanotube is 0.34 nm, and the interference fringes have a spacing of 0.58 nm. The lattice image of the graphite layers and the electron interference fringes are recorded at a mutual angle of 20°. FIG. 10(C) shows a phase image reconstructed from the hologram in FIG. 10(A). Both the carbon nanotube and the iron particles are clearly reconstructed. FIGS. 10(D) and 10(E) are phase profiles along an arrowed position D-D (the position in which the iron particles are exist) and a portion E-E (the position of carbon nanotube only) shown in FIG. 10(C). Here, the experimental result is indicated by a solid line and the theoretical result is indicated by a dashed line. In FIG. 10(D), the phase profile is outstandingly increased as the iron particles are included in the carbon nanotube. In FIG. 10(E), as only the carbon nanotube including no particles is shown, the phase profile with a dent in the center portion is found to be formed corresponding to decrease in the projected thickness at the hollow portion of the tube. The bore and outer diameters of the tube are found from FIG. 10(A). Based on this, the phase profile of an electron wave passed through the nanotube can be calculated. The theoretical results shown in FIGS. 10(D) and 10(E) are obtained by this calculation. As shown in the figures, the experimental results are in good agreement with the calculation. For this calculation, the mean inner potential of a material need to be used as a parameter. Fitting the theoretical calculations with the experimental results can determine the mean inner potentials of carbon graphite and iron. The value of mean-inner-potential of the carbon graphite is 10.8V and the value of mean-inner-potential of iron is 25.0V, respectively. The measured values of the mean inner potentials are in good agreement with other experimental results and theoretical calculations.

According to the technology disclosed herein, the azimuth θ as a new parameter can be introduced into the conventional electron holography in a controllable form. Furthermore the concept about interference of the electron holography is extended to a two-dimensional plane. According to the present invention, the following functions and effects can be expected.

(1) Formation of Interference Fringes Having an Arbitrary Azimuth within an Obtained Interference Area The optimum interference area is formed according to an observation object such as the shape of a specimen, the shape of a portion to be observed, and the orientation of a lattice image. Furthermore the interference fringes with the optimum azimuth are superimposed to the observation object independently. A hologram can be formed and recorded in the optimum state in spatial resolution and phase resolution.

(3) Extension of the Concept of the Electron Holography to Two Dimensions

The prior art of the conventional electron holography uses a filament electrode in a one-dimensional shape and treats an interference phenomenon only in the vertical direction for the filament electrode. According to the technology disclosed herein, in principle, an electron wavefront in any portions in a two-dimensional plane can be superimposed on each other to interfere. Conceptually, the conventional electron holography is extended to two dimensions. The specific effects include (i) measurement of two-dimensional distribution of degree of coherence in electron waves, (ii) improvement in the S/N ratio of a hologram using an optimum area as a reference wave, and (iii) reduction in constraint on the shape of a specimen. The experimental efficiency of the holography can be expected to be improved.

(Application to the Interferometer Using Light Beam)

Figure 11:
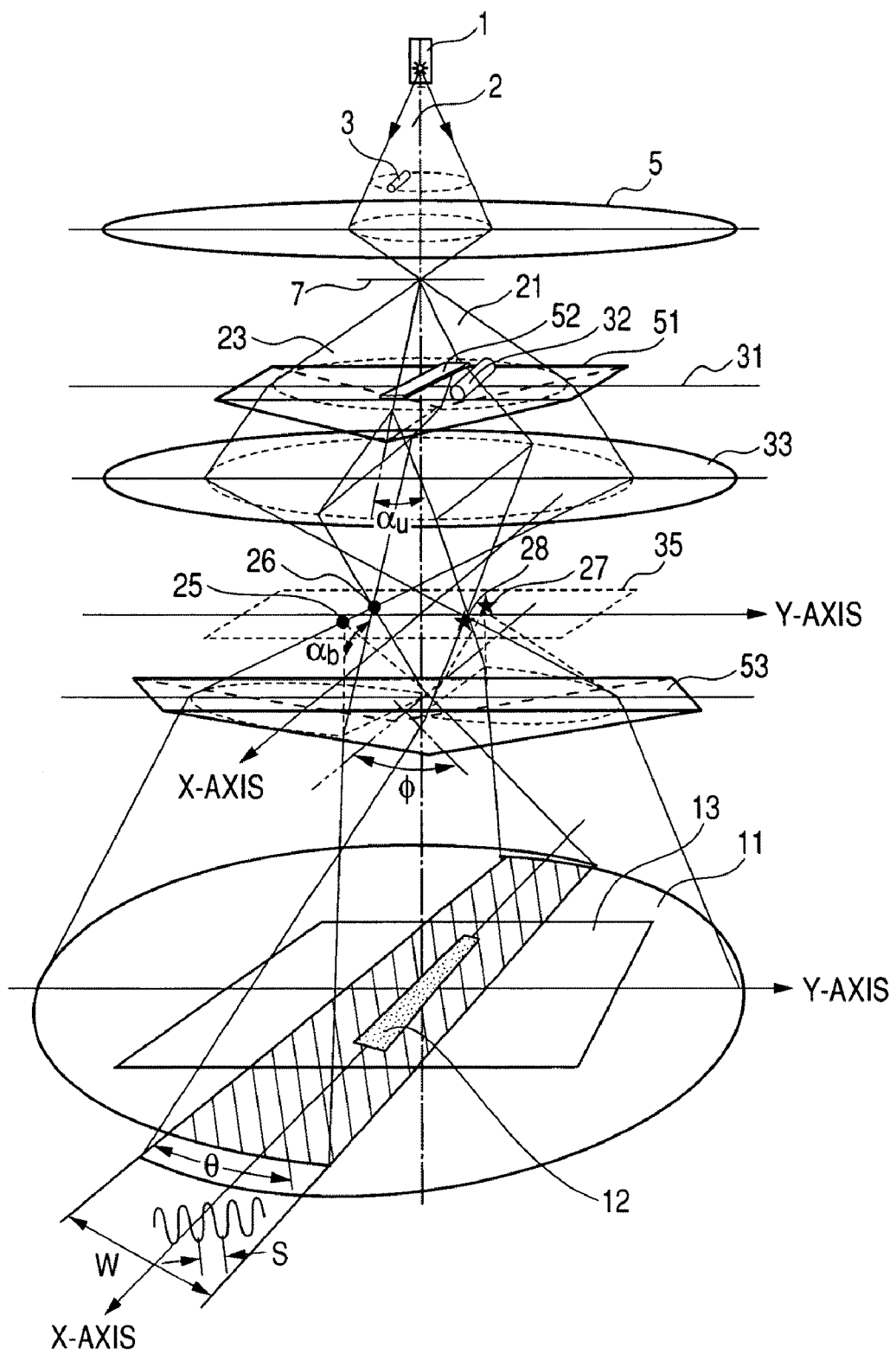
FIG. 11 is a schematic diagram showing, corresponding to FIG. 2, an interference optical system in which the technology disclosed herein is applied to an optical interferometer using light beam.

The interferometer using an electron beam is mainly described above. As described in Japanese Patent Application No. 2004-004156, the technology disclosed herein also can be embodied in the optical interferometer using light beam. FIG. 11 shows, corresponding to FIG. 2, an optical system in which the technology disclosed herein is applied to the optical interferometer using light beam. As easily seen by comparing FIG. 2 with FIG. 11, simply, the upper-stage and lower-stage electron biprisms $9u$ and $9b$ are replaced with optical biprisms 51 and 53 and a beam stopper 52 for intercepting light beam is provided in the center position of the optical biprism 51. The optical biprism 53 is rotated in such a manner that the relative azimuth angle of the ridge lines of the optical biprisms 51 and 53 is changed, which is the same control as rotation of the filament electrode $9b$ of the lower-stage electron biprism, As described in Japanese Patent Application No. 2004-004156, generally, the optical biprism cannot change deflection angle α by controlling a voltage, unlike the electron biprism. The optical biprism need to be replaced according to the interference fringe spacing s and the interference area width W is required. The use is troublesome. With regard to this, a case in an optical biprism shape by glass is made and a gas is filled in it so that its pressure can be changed, that is, the mass density can be changed. The refraction factor of the optical biprism is changed to perform arbitral angle deflection. The reflection angles of two mirrors in place of one biprism are controlled to expect the same effect as the electron biprism (for instance, K. Harada, K. Ogai and R. Shimizu: Technology Reports of The Osaka University 39, 117 (1989)).

INDUSTRIAL APPLICABILITY

According to the technology disclosed herein, in addition to independent control of two parameters of the interference area width W and the interference fringe spacing s, it is possible to realize the interferometer which can easily observe the specimen in the longitudinal direction by controlling the azimuth θ of the interference fringes.

EXPLANATION OF REFERENCE NUMERALS AND SYMBOLS

1 . . . electron source,
2 . . . optical axis,
3 . . . specimen,
5 . . . objective lens system (a system having one or more lenses is represented by one equivalent lens),
7 . . . first image plane of an electron source,
$9_u$ . . . filament electrode of an upper-stage electron biprism,
$9_b$ . . . filament electrode of a lower-stage electron biprism,
11 . . . observation plane,
11' . . . image plane of a specimen by a magnifying lens 33,
12 . . . specimen image on the observation plane 11,
13 . . . image recording means such as a film or camera,
21 . . . object wave,
23 . . . reference wave,
25, 27 . . . virtual image of the electron source on the second image plane of the electron source 35,
26, 28 . . . real image of the electron source on the second image plane of the electron source 35,
31 . . . first image plane just behind the objective lens system 5,
32 . . . specimen image on the first image plane 31,
33 . . . magnifying lens,
35 . . . second image plane of the electron source,
41 . . . second magnifying lens,
42 . . . third magnifying lens,
43 . . . projection lens,
51, 53 . . . optical biprism,
52 . . . beam stopper,
$a_{Obj}$ . . . distance between the objective lens system 5 and the specimen 3 (equivalent distance),
$b_{Obj}$ . . . distance between the objective lens 5 and the first image plane 31 (equivalent distance),
$a_M$ . . . distance between the magnifying lens 33 and the first image plane 31,
$b_M$ . . . distance between the magnifying lens 33 and the observation plane 11,
$a_1$ . . . distance between the objective lens system 5 and the electron source 1 (equivalent distance),
$b_1$ . . . distance between the objective lens system 5 and the first image plane of the electron source 7 (equivalent distance),
$a_2$ . . . distance between the magnifying lens 33 and the first image plane of the electron source 7,
$b_2$ . . . distance between the magnifying lens 33 and the second image plane of the electron source 35,
λ . . . wavelength of an electron beam from the electron source 1,
$α_u$ . . . deflection angle of the electron beam by the upper-stage electron biprism $9_u$,
$α_b$ . . . deflection angle of the electron beam by the lower-stage electron biprism $9_b$,
$M_{Obj}$ . . . magnification by the objective lens system 5,
$M_M$ . . . magnification by the magnifying lens 33,
$D_u$ . . . distance between the first image plane of the electron source 7 and the first image plane 31,
$D_b$ . . . distance between the second image plane of the electron source 35 and the observation plane 11,
$L_b$ . . . distance between the lower-stage electron biprism $9_b$ and the observation plane 11,
$d_u$ . . . diameter of the filament electrode $9_u$ of the upper-stage electron biprism,
$d_b$ . . . diameter of the filament electrode $9_b$ of the lower-stage electron biprism, $V_u$ ... applied voltage to the filament electrode $9_u$ of the upper-stage electron biprism, $V_b$ ... applied voltage to the filament electrode $9_b$ of the lower-stage electron biprism

The invention claimed is:

1. A charged particle beam apparatus comprising:
    a source of a charged particle beam such as an electron or an ion;
    a condenser optical system for irradiating a specimen with the charged particle beam emitted from the source;
    a specimen holder for holding the specimen irradiated with the charged particle beam;
    an imaging lens system for imaging the specimen;
    a device for observing or recording the specimen image;
    an objective lens system formed by one or plurality of lenses capable of controlling focal lengths independently in the imaging lens system positioned on the downstream side on the traveling direction of the charged particle beam from the specimen position on an optical axis of the charged particle beam;
    an upper-stage biprism located in a plane orthogonal to the optical axis at a position of an image plane of the specimen determined by the objective lens system on the downstream side of the objective lens system; and
    a lower-stage biprism located in a plane in parallel with the plane where the upper-stage biprism is placed on the downstream side of the upper-stage biprism through one or more lenses in the imaging lens system,
    both the biprisms being capable of moving of their positions and rotating of their electrodes independently, wherein voltages can be applied to the upper-stage biprism and the lower-stage biprism independently to deflect the charged particle beam in an arbitrary direction, and
    wherein in a case that an azimuth angle between the upper-stage biprism and the lower-stage biprism is $\Phi$, and an azimuth angle between the upper-stage biprism and interference fringes is $\theta$, the charged particle beam is deflected in condition that the azimuth angle $\Phi$ is not zero for controlling the azimuth angle $\theta$.

2. The charged particle beam apparatus according to claim 1,
    wherein: the specimen image formed in an arbitrary magnification in a plane where the upper-stage biprism is positioned with orthogonal to the optical axis by adjusting the respective lenses of the objective lens system having the plurality of lenses.

3. The charged particle beam apparatus according to claim 1,
    wherein the lower-stage biprism is positioned on the downstream side of an image plane of the source determined by a lens on the downstream side of the lens positioned on the downstream side of the upper-stage biprism on the optical axis of the charged particle beam system.

4. The charged particle beam apparatus according to claim 1,
    wherein the lower-stage biprism is positioned between a lens and an image plane of the source determined by the lens on the downstream side of the lens positioned on the downstream side of the upper-stage biprism on the optical axis of the charged particle beam system.

5. An interferometer comprising:
    a light source of light beam;
    a condenser optical system for irradiating a specimen with a light beam emitted from the light source;
    a specimen holder for holding the specimen irradiated with the light beam;
    an imaging lens system for imaging the specimen;
    a device for observing or recording the specimen image;
    an upper-stage optical biprism located in a plane orthogonal to an optical axis at a position of an image plane of the specimen determined by the objective lens on the downstream side of an objective lens positioned on the downstream side in the traveling direction of the light beam from the specimen position on the optical axis of the light beam and having a beam stopper of the light beam arranged in a center ridge line portion or the back side of the ridge line; and
    a lower-stage optical biprism located in a plane in parallel with the plane where the upper-stage optical biprism is placed on the downstream side of the upper-stage optical biprism through one or more lenses of the imaging lens system, both the optical biprisms being capable of moving of their positions and rotating of their electrodes independently, to deflect the light beam in an arbitrary direction,
    wherein the upper-stage optical biprism and the lower-stage optical biprism are replaced with ones having different deflection angles to the light beam independently to control the deflection angles; and
    wherein in a case that an azimuth angle between the upper-stage biprism and the lower-stage biprism is $\Phi$, and an azimuth angle between the upper-stage biprism and interference fringes is $\theta$, the light beam is deflected in condition that the azimuth angle $\Phi$ is not zero for controlling the azimuth angle $\theta$.

6. The charged particle beam apparatus according to claim 1, wherein the upper-stage biprism comprises an upper-stage filament electrode and the lower-stage biprism comprises a lower-stage filament electrode, and wherein the azimuth angle $\Phi$ exists between axes of the upper-stage filament electrode and the lower-stage filament electrode.

7. The interferometer according to claim 5, wherein the azimuth angle $\Phi$ exists between a ridge line of the upper-stage optical prism and a ridge line of the lower-stage optical prism.

8. A method of operating a charged particle beam apparatus comprising:
    irradiating a specimen with a charged particle beam, the charged particle beam having an optical axis;
    imaging the specimen;
    using an imaging lens system comprising an objective lens system, an upper-stage biprism, and a lower-stage biprism for obtaining interference infringes in an observation plane;
    the upper-stage biprism being located in a plane orthogonal to the optical axis at a position of an image plane of the specimen determined by the objective lens system on a downstream side of the objective lens system;
    the lower-stage biprism being located in a plane in parallel with the plane where the upper-stage biprism is placed on the downstream side of the upper-stage biprism through one or more lenses in the imaging lens system;
    both the biprisms being capable of moving of their positions and rotating of their electrodes independently, wherein voltages can be applied to the upper-stage biprism and the lower-stage biprism independently to deflect the charged particle beam in an arbitrary direction, and
    deflecting the charged particle beam by using a non-zero azimuth angle $\theta$ between the upper-stage biprism and the lower-stage biprism and thereby controlling an azi muth angle θ between the upper-stage biprism and interference fringes.

9. The method according to claim 8, wherein the upper-stage biprism comprises an upper-stage filament electrode and the lower-stage biprism comprises a lower-stage filament electrode, and wherein the azimuth angle Φ exists between axes of the upper-stage filament electrode and the lower-stage filament electrode.

* * * * *